United States Patent [19]
McKenzie

[11] Patent Number: 6,121,461
[45] Date of Patent: Sep. 19, 2000

[54] **FORM III CRYSTALLINE [R-(R*,R*)]-2-(4-FLUOROPHENYL)-β,δ-DIHYDROXY-5-(1-METHYLETHYL)-3-PHENYL-4-[(PHENYLAMINO) CARBONYL]-1H-PYRROLE-1-HEPTANOIC ACID CALCIUM SALT (2:1)**

[75] Inventor: Ann T. McKenzie, West Lafayette, Ind.

[73] Assignee: Warner-Lambert Company, Morris Plains, N.J.

[*] Notice: This patent is subject to a terminal disclaimer.

[21] Appl. No.: 09/360,778

[22] Filed: Jul. 26, 1999

Related U.S. Application Data

[63] Continuation of application No. 08/945,817, filed as application No. PCT/US96/11367, Jul. 8, 1996, abandoned
[60] Provisional application No. 60/001,454, Jul. 17, 1995.

[51] Int. Cl.[7] .................. C07D 207/327; C07D 207/333; C07D 207/335
[52] U.S. Cl. .................. 548/530; 548/537; 548/560; 548/561; 548/562
[58] Field of Search ..................... 548/530, 537, 548/560, 561, 562; 514/423, 427, 428

[56] References Cited

U.S. PATENT DOCUMENTS 5,316,765   5/1994   Folkers et al. .................. 424/94.1

FOREIGN PATENT DOCUMENTS

| 0409281 | 7/1990 | European Pat. Off. . |
| 0 409281 | 1/1991 | Germany . |
| WO 94/16693 | 8/1994 | WIPO . |
| 9416693 | 8/1995 | WIPO . |

OTHER PUBLICATIONS

*Tetrahedron Letters*, vol. 33, No. 17, 1992, pp. 2283–2284, Baumann, et al.
*Pharmaceutical Research*, vol. 10, No. 10, 1993, pp. 1461–1465, Kearney, et al.
*Atherosclerosis*, vol. 111, 1994, pp. 127–142, Bocan, et al.
*Tetrahedron Letters*, vol.33, No. 17, 1992, pp 2283–2284, Baumann, et al.
*Pharmaceutical Research*, vol. 10, No. 10, 1993, pp 1461–1465, Kearney, et al.

Primary Examiner—Joseph McKane
Assistant Examiner—Jane C. Osuecki
Attorney, Agent, or Firm—Francis J. Tinney

[57] ABSTRACT

A novel crystalline form of [(R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt designated Form III is characterized by its X-ray powder diffraction and/or solid state NMR is described, as well as methods for the preparation and pharmaceutical composition of the same, which is useful as an agent for treating hyperlipidemia and hypercholesterolemia.

9 Claims, 2 Drawing Sheets

FORM III CRYSTALLINE [R-(R*,R*)]-2-(4-FLUOROPHENYL)-β,δ-DIHYDROXY-5-(1-METHYLETHYL)-3-PHENYL-4-[(PHENYLAMINO) CARBONYL]-1H-PYRROLE-1-HEPTANOIC ACID CALCIUM SALT (2:1)

This application is a continuation of Ser. No. 08/945,817, filed Sep. 29, 1997, which is a 371 of PCT/US96/11367, filed Jul. 8, 1996, and claims benefit of provisional application 60/001454, filed Jul. 17, 1995.

BACKGROUND OF THE INVENTION

The present invention relates to a novel crystalline form of atorvastatin which is known by the chemical name [R-(R*,R*)]-2-(4-fluorophenyl)-β, δ-dihydroxy-5-(1-methylethyl)-3-phenyl-4-[(phenylamino)carbonyl]-1H-pyrrole-1-heptanoic acid hemi calcium salt useful as a pharmaceutical agent, to methods for its production and isolation, to pharmaceutical compositions which include this compound and a pharmaceutically acceptable carrier, and to pharmaceutical methods of treatment. The novel crystalline compound of the present invention is useful as an inhibitor of the enzyme 3-hydroxy-3-methylglutaryl-coenzyme A reductase (HMG—CoA reductase) and is thus useful as a hypolipidemic and hypocholesterolemic agent.

U.S. Pat. No. 4,681,893, which is herein incorporated by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide.

U.S. Pat. No. 5,273,995, which is herein incorporated by reference, discloses the enantiomer having the R form of the ring-opened acid of trans-5-(4-fluorophenyl)-2-(1-methylethyl)-N,4-diphenyl-1-[(2-tetrahydro-4-hydroxy-6-oxo-2H-pyran-2-yl)ethyl]-1H-pyrrole-3-carboxamide, i.e., [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid.

U.S. Pat. Nos. 5,003,080; 5,097,045; 5,103,024; 5,124,482; 5,149,837; 5,155,251; 5,216,174; 5,245,047; 5,248,793; 5,280,126; 5,397,792; and 5,342,952, which are herein incorporated by reference, disclose various processes and key intermediates for preparing atorvastatin.

Atorvastatin is prepared as its calcium salt, i.e., [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1). The calcium salt is desirable since it enables atorvastatin to be conveniently formulated in, for example, tablets, capsules, lozenges, powders, and the like for oral administration. Additionally, there is a need to produce atorvastatin in a pure and crystalline form to enable formulations to meet exacting pharmaceutical requirements and specifications.

Furthermore, the process by which atorvastatin is produced needs to be one which is amenable to large-scale production. Additionally, it is desirable that the product should be in a form that is readily filterable and easily dried. Finally, it is economically desirable that the product be stable for extended periods of time without the need for specialized storage conditions.

The processes in the above United States patents disclose amorphous atorvastatin which has unsuitable filtration and drying characteristics for large-scale production and must be protected from heat, light, oxygen, and moisture.

We have now surprisingly and unexpectedly found that atorvastatin can be prepared in crystalline form. Thus, the present invention provides atorvastatin in a new crystalline form designated Form III. Form III atorvastatin has different physical characteristics compared to the previous amorphous product.

SUMMARY OF THE INVENTION

Accordingly, the present invention is directed to crystalline Form III atorvastatin and hydrates thereof characterized by the following X-ray powder diffraction pattern expressed in terms of the 2θ, d-spacings, and relative intensities with a relative intensity of >25% measured on a Siemens D-500 diffractometer with CuK$_\alpha$ radiation:

| 2θ | d | Relative Intensity (>25%) |
|---|---|---|
| 4.123 | 21.4140 | 49.20 |
| 4.993 | 17.6832 | 30.82 |
| 5.768 | 15.3099 | 28.69 |
| 7.670 | 11.5173 | 25.49 |
| 8.451 | 10.4538 | 100.00 |
| 15.962 | 5.5478 | 32.59 |
| 16.619 | 5.3298 | 62.34 |
| 17.731 | 4.9981 | 49.29 |
| 18.267 | 4.8526 | 45.12 |
| 18.870 | 4.6989 | 39.52 |
| 19.480 | 4.5531 | 36.59 |
| 19.984 | 4.4393 | 70.34 |
| 20.294 | 4.3722 | 69.54 |
| 21.105 | 4.2061 | 37.39 |
| 21.670 | 4.0976 | 36.50 |
| 23.318 | 3.8117 | 38.63 |
| 24.405 | 3.6442 | 65.54 |
| 24.967 | 3.5635 | 27.20 |
| 25.397 | 3.5041 | 33.75 |

Further, the present invention is directed to crystalline Form III atorvastatin and hydrates thereof characterized by the following solid-state $^{13}$C nuclear magnetic resonance spectrum wherein chemical shift is expressed in parts per million measured on a Bruker AX-250 spectrometer:

| Assignment | Chemical Shift |
|---|---|
| Spinning Side Band | 214.8 |
| | 209.3 |
| | 202.3 |
| C12 or C25 | 184.9 |
| C12 or C25 | 166.7 |
| C16 | 161.0 (weak, broad) |
| Aromatic Carbons | |
| C2–C5, C13–C18, C19–C24, C27–C32 | 140.1 |
| | 135.2 |
| | 131.8 |
| | 128.9 |
| | 124.3 |
| | 122.2 |
| | 117.2 |
| | 114.9 |
| C8, C10 | 69.8 |
| | 67.3 |
| | 65.6 |
| Methylene Carbons | |
| C6, C7, C9, C11 | 44.1 |
| | 40.4 |
| | 35.4 |

-continued

| Assignment | Chemical Shift |
|---|---|
| C33 | 27.0 |
|  | 24.1 |
| C34 | 22.1 |
|  | 19.9 |

As an inhibitor of HMG—CoA, the novel crystalline form of atorvastatin is useful as a hypolipidemic and hypocholesterolemic agent.

A still further embodiment of the present invention is a pharmaceutical composition for administering an effective amount of crystalline Form III atorvastatin in unit dosage form in the treatment methods mentioned above. Finally, the present invention is directed to methods for production of Form III atorvastatin.

BRIEF DESCRIPTION OF THE DRAWINGS

The invention is further described by the following non-limiting examples which refer to the accompanying FIGS. 1 to 2, short particulars of which are given below.

Figure 1:
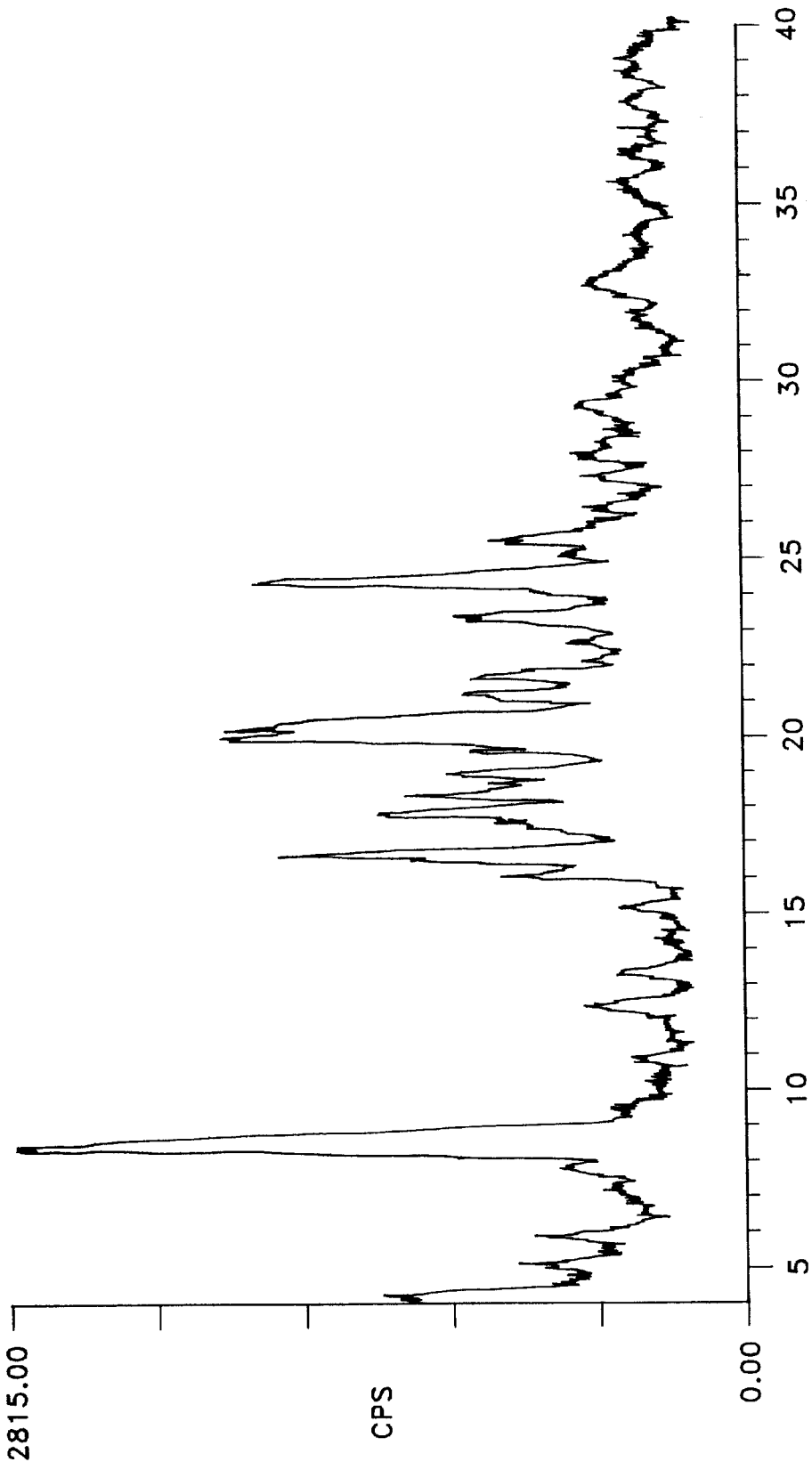
FIG. 1
Figure 2:
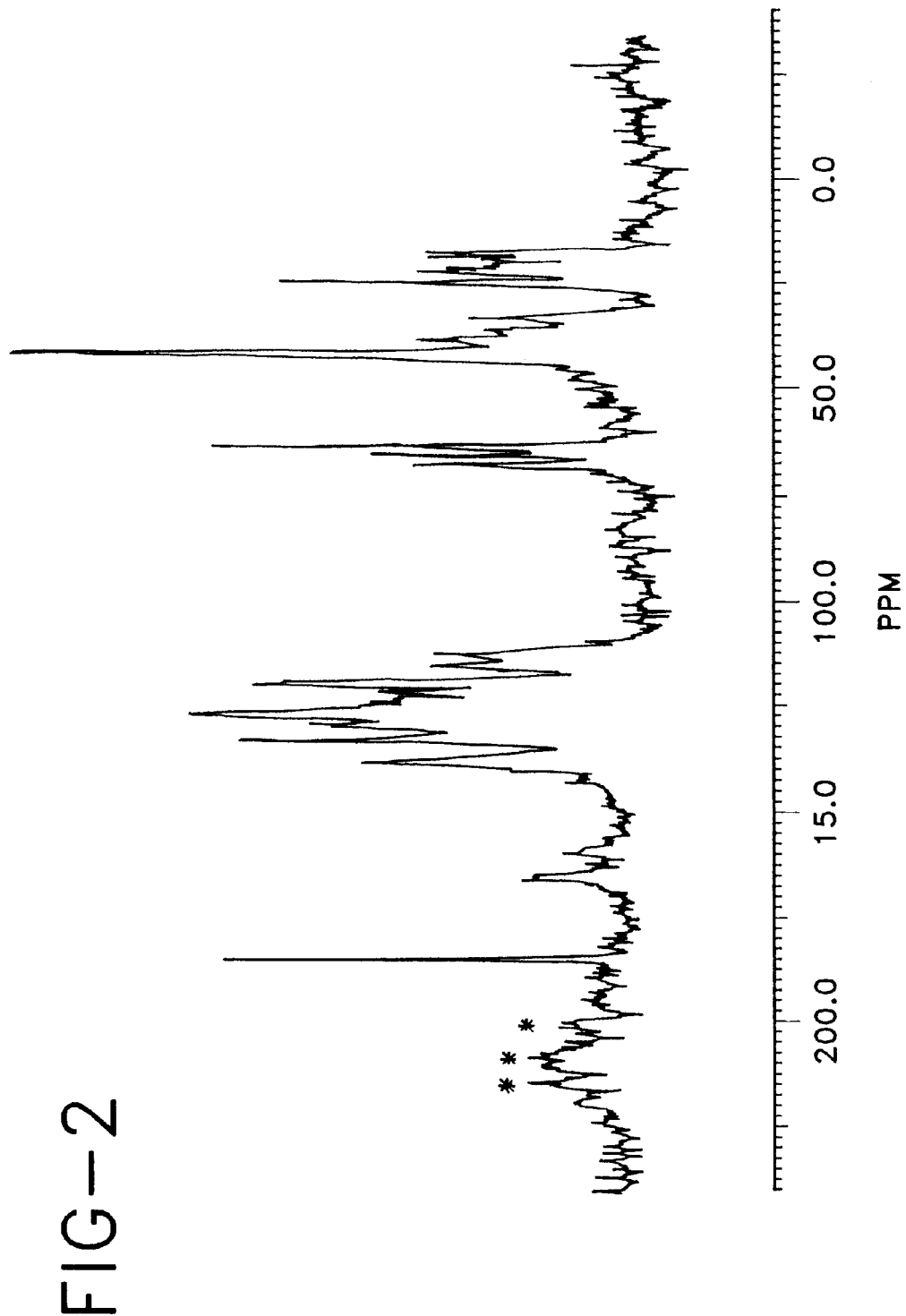

Diffractogram of Form III atorvastatin (Y-axis=0 to maximum intensity of 2815 counts per seconds (cps)).

FIG. 2

Solid-state $^{13}C$ nuclear magnetic resonance spectrum with spinning side bands identified by an asterisk of Form III atorvastatin.

DETAILED DESCRIPTION OF THE INVENTION

Crystalline Form III atorvastatin may be characterized by its X-ray powder diffraction pattern and/or by its solid state nuclear magnetic resonance spectra (NMR).

X-Ray Powder Diffraction

Form III Atorvastatin

Form III atorvastatin was characterized by its X-ray powder diffraction pattern. Thus, the X-ray diffraction pattern of Form III atorvastatin was measured on a Siemens D-500 diffractometer with $CuK_a$ radiation.

Equipment

Siemens D-500 Diffractometer-Kristalloflex with an IBM-compatible interface, software=DIFFRAC AT (SOCABIM 1986, 1992).

$CuK_a$ radiation (20 mA, 40 kV, λ=1.5406 Å) Slits I and II at 1°) electronically filtered by the Kevex Psi Peltier Cooled Silicon [Si(Li)]Detector (Slits: III at 1° and IV at 0.15°).

Methodology

The silicon standard is run each day to check the X-ray tube alignment.

Continuous θ/2θ coupled scan: 4.00° to 40.00° in 2θ, scan rate of 6°/min: 0.4 sec/0.04° step.

Sample tapped out of vial and pressed onto zero-background quartz in Al holder. Sample width 13–15 mm.

Samples are stored and run at room temperature.

Table 1 lists the 2θ, d-spacings, and relative intensities of all lines in the unground sample with a relative intensity of >25% for crystalline Form III atorvastatin. It should also be noted that the computer-generated unrounded numbers are listed in this table.

TABLE 1

Intensities and Peak Locations of All Diffraction Lines With Relative Intensity Greater Than 25% for Form III Atorvastatin

| 2θ | d | Relative Intensity (>25%) |
|---|---|---|
| 4.123 | 21.4140 | 49.20 |
| 4.993 | 17.6832 | 30.82 |
| 5.768 | 15.3099 | 28.69 |
| 7.670 | 11.5173 | 25.49 |
| 8.451 | 10.4538 | 100.00 |
| 15.962 | 5.5478 | 32.59 |
| 16.619 | 5.3298 | 62.34 |
| 17.731 | 4.9981 | 49.29 |
| 18.267 | 4.8526 | 45.12 |
| 18.870 | 4.6989 | 39.52 |
| 19.480 | 4.5531 | 36.59 |
| 19.984 | 4.4393 | 70.34 |
| 20.294 | 4.3722 | 69.54 |
| 21.105 | 4.2061 | 37.39 |
| 21.670 | 4.0976 | 36.50 |
| 23.318 | 3.8117 | 38.63 |
| 24.405 | 3.6442 | 65.54 |
| 24.967 | 3.5635 | 27.20 |
| 25.397 | 3.5041 | 33.75 |

Solid State Nuclear Magnetic Resonance (NMR)

Methodology

All solid-state $^{13}C$ NMR measurements were made with a Bruker AX-250, 250 MHz NMR spectrometer. High resolution spectra were obtained using high-power proton decoupling and cross-polarization (CP) with magic-angle spinning (MAS) at approximately 5 kHz. The magic-angle was adjusted using the Br signal of KBr by detecting the side bands as described by Frye and Maciel (Frye J. S. and Maciel G. E., *J. Mag. Res.*, 1982;48:125). Approximately 300 to 450 mg of sample packed into a canister-design rotor was used for each experiment. Chemical shifts were referenced to external tetrakis (trimethylsilyl)silane (methyl signal at 3.50 ppm) (Muntean J. V. and Stock L. M., *J. Mag. Res.*, 1988;76:54).

Table 2 shows the solid-state NMR spectrum for crystalline Form III atorvastatin.

TABLE 2

Carbon Atom Assignment and Chemical Shift for Form III Atorvastatin

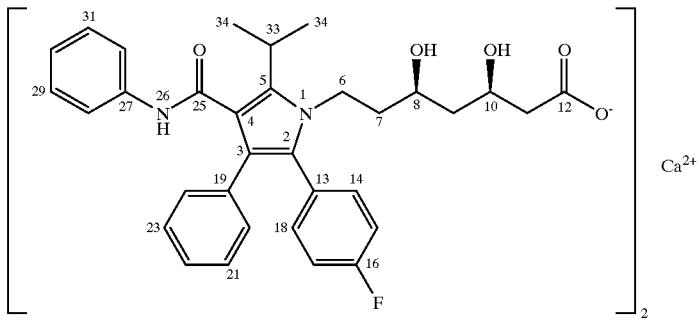

| Assignment | Chemical Shift |
|---|---|
| Spinning Side Band | 214.8 |
|  | 209.3 |
|  | 202.3 |
| C12 or C25 | 184.9 |
| C12 or C25 | 166.7 |
| C16 | 161.0 (weak, broad) |
| Aromatic Carbons C2–C5, C13–C18, C19–C24, C27–C32 | 140.1 |
|  | 135.2 |
|  | 131.8 |
|  | 128.9 |
|  | 124.3 |
|  | 122.2 |
|  | 117.2 |
|  | 114.9 |
| C8, C10 | 69.8 |
|  | 67.3 |
|  | 65.6 |
| Methylene Carbons C6, C7, C9, C11 | 44.1 |
|  | 40.4 |
|  | 35.4 |
| C33 | 27.0 |
|  | 24.1 |
| C34 | 22.1 |
|  | 19.9 |

Crystalline Form III atorvastatin of the present invention can exist in anhydrous form as well as hydrated forms. In general, the hydrated forms, are equivalent to unhydrated forms and are intended to be encompassed within the scope of the present invention.

The present invention also provides a process for the preparation of crystalline Form III atorvastatin which comprises exposing atorvastatin to a high relative humidity under conditions which yield crystalline Form III atorvastatin.

The precise conditions under which Form III of crystalline atorvastatin is formed may be empirically determined and it is only possible to give a method which has been found to be suitable in practice.

Thus, for example, when the starting material is Form II of crystalline atorvastatin disclosed in concurrently filed United States patent application titled "Crystalline [R-(R*, R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1)" commonly owned, attorney's Case Number PD-5250-01-FJT, Ser. No. 08/945,812 (Crystalline Form I and Form IV atorvastatin are also disclosed in this application), the desired Form III of crystalline atorvastatin may be obtained by exposing the solid to a relative humidity of 95% for 11 days.

Crystalline Form II atorvastatin may be prepared from amorphous, a combination of amorphous and crystalline Form I atorvastatin or crystalline Form I atorvastatin. Thus, for example, when the starting material is amorphous, a combination of amorphous and Form I, or crystalline Form I atorvastatin, the desired Form II of crystalline atorvastatin may be obtained by suspending the solid in methanol containing about 40% to about 50% water until conversion to the required form is complete, followed by filtration.

Crystalline Form I atorvastatin may be prepared by crystallization under controlled conditions. In particular, it can be prepared either from an aqueous solution of the corresponding basic salt such as, an alkali metal salt, for example, lithium, potassium, sodium, and the like; ammonia or an amine salt; preferably, the sodium salt by addition of a calcium salt, such as, for example, calcium acetate and the like, or by suspending amorphous atorvastatin in water. In general, the use of a hydroxylic co-solvent such as, for example, a lower alkanol, for example methanol and the like, is preferred.

The compound of the present invention can be prepared and administered in a wide variety of oral and parenteral dosage forms. Thus, the compound of the present invention can be administered by injection, that is, intravenously, intramuscularly, intracutaneously, subcutaneously, intraduodenally, or intraperitoneally. Also, the compound of the present invention can be administered by inhalation, for example, intranasally. Additionally, the compound of the present invention can be administered transdermally. It will be obvious to those skilled in the art that the following dosage forms may comprise as the active component, either compounds or a corresponding pharmaceutically acceptable salt of the compound of the present invention.

For preparing pharmaceutical compositions from the compound of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from two or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, retention enemas, and emulsions, for example water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.5 mg to 100 mg, preferably 2.5 mg to 80 mg according to the particular application and the potency of the active component. The composition can, if desired, also contain other compatible therapeutic agents.

In therapeutic use as a hypolipidemic and/or hypocholesterolemic agent, crystalline Form III atorvastatin utilized in the pharmaceutical method of this invention is administered at the initial dosage of about 2.5 mg to about 80 mg daily. A daily dose range of about 2.5 mg to about 20 mg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired.

The following nonlimiting examples illustrate the inventors' preferred methods for preparing the compounds of the invention.

EXAMPLE 1

[R-(R*,R*)]-2-(4-Fluorophenyl)-β,δ-dihydroxy-5-(1-methylethyl)-3-phenyl-4-[(phenylamino) carbonyl]-1H-pyrrole-1-heptanoic acid hemi calcium salt (Form I Atorvastatin)

A mixture of (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide (atorvastatin lactone) (U.S. Pat. No. 5,273,995) (75 kg), methyl tertiary-butyl ether (MTBE) (308 kg), methanol (190 L) is reacted with an aqueous solution of sodium hydroxide (5.72 kg in 950 L) at 48–58° C. for 40 to 60 minutes to form the ring-opened sodium salt. After cooling to 25–35° C., the organic layer is discarded, and the aqueous layer is again extracted with MTBE (230 kg). The organic layer is discarded, and the MTBE saturated aqueous solution of the sodium salt is heated to 47–52° C. To this solution is added a solution of calcium acetate hemihydrate (11.94 kg) dissolved in water (410 L), over at least 30 minutes. The mixture is seeded with a slurry of crystalline Form I atorvastatin (1.1 kg in 11 L water and 5 L methanol) shortly after addition of the calcium acetate solution. The mixture is then heated to 51–57° C. for at least 10 minutes and then cooled to 15–40° C. The mixture is filtered, washed with a solution of water (300 L) and methanol (150 L) followed by water (450 L). The solid is dried at 60–70° C. under vacuum for 3 to 4 days to give crystalline Form I atorvastatin (72.2 kg).

EXAMPLE 2

[R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt (Form II Atorvastatin)

A mixture of amorphous and crystalline Form I atorvastatin (100 g) was suspended in a mixture of methanol (1200 mL) and water (800 mL) and stirred for 3 days. The material was filtered, dried at 70° C. under reduced pressure to give crystalline Form II atorvastatin.

EXAMPLE 3

[R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid hemi calcium salt
(Form III Atorvastatin)

Form II atorvastatin (Example 2) is rotapped through a 50 mesh screen onto a 100 mesh screen and exposed in a humidity jar to 95% relative humidity for 11 days to afford crystalline Form III atorvastatin.

What is claimed is:

1. Crystalline Form III atorvastatin hydrate having an X-ray powder diffraction having at least one of the following 2θ values measured using CuK$_\alpha$ radiation: 16.6 or 20.0.

2. Crystalline Form III atorvastatin hydrate having an X-ray powder diffraction having the following 2θ values measured using CuK$_\alpha$ radiation: 16.6, 20.0 and 20.3.

3. Crystalline Form III atorvastatin hydrate having an X-ray powder diffraction having the following 2θ values measured using CuK$_\alpha$ radiation: 8.5, 16.6 and 24.4.

4. Crystalline Form III atorvastatin hydrate having an X-ray powder diffraction having the following 2θ values measured using CuK$_\alpha$ radiation: 4.1, 5.0, 5.8, 7.7, 8.5, 16.0, 16.6, 17.7, 18.3, 18.9, 19.5, 20.0, 20.3, 21.1, 21.7, 23.3, 24.4, 25.0 and 25.4.

5. Crystalline Form III atorvastatin hydrate having an X-ray powder diffraction having the following 2θ values measured using CuK$_\alpha$ radiation: 4.123, 4.993, 5.768, 7.670, 8.451, 15.962, 16.619, 17.731, 18.267, 18.870, 19.480, 19.984, 20.294, 21.105, 21.670, 23.318, 24.405, 24.967 and 25.397.

6. Crystalline Form III atorvastatin hydrate characterized by solid state $^{13}$C nuclear magnetic resonance having a chemical shift difference between the lowest ppm resonance and another resonance of 7.1 or 165.0.

7. Crystalline Form III atorvastatin hydrate characterized by solid state $^{13}$C nuclear magnetic resonance having the following chemical shift differences between the lowest ppm resonance and other resonances: 2.2, 4.2, 7.1, 45.7, 47.4 and 165.0.

8. Crystalline Form III atorvastatin hydrate characterized by solid state $^{13}$C nuclear magnetic resonance having the following chemical shift differences between the lowest ppm resonance and other resonances: 2.2, 4.2, 7.1, 15.5, 20.5, 24.2, 45.7, 47.4, 49.9, 95.0, 97.3, 102.3, 104.4, 109.0, 111.9, 115.3, 120.2, 141.1, 146.8 and 165.0.

9. Crystalline Form III atorvastatin hydrate characterized by solid state $^{13}$C nuclear magnetic resonance having the following chemical shifts expressed in parts per million: 19.9, 22.1, 24.1, 27.0, 35.4, 40.4, 44.1, 65.6, 67.3, 69.8, 114.9, 117.2, 122.2, 124.3, 128.9, 131.8, 135.2, 140.1, 161.0, 166.7 and 184.9.

* * * * *